United States Patent [19]

Van Horn

[11] Patent Number: 4,917,769

[45] Date of Patent: Apr. 17, 1990

[54] DISTILLATION APPARATUS FOR REMOVAL OF VOLATILE ACIDS FROM AQUEOUS SOLUTIONS

[75] Inventor: Wendell E. Van Horn, Chicago, Ill.

[73] Assignee: OO Chemicals, Inc., West Lafayette, Ind.

[21] Appl. No.: 356,549

[22] Filed: May 24, 1989

Related U.S. Application Data

[62] Division of Ser. No. 189,228, May 2, 1988, Pat. No. 4,898,644.

[51] Int. Cl.⁴ .............................................. B01D 3/32
[52] U.S. Cl. .................... 202/158; 202/197; 202/234; 203/96; 203/DIG. 6; 203/DIG. 9; 422/189; 422/195
[58] Field of Search ............... 202/158, 197, 172, 159, 202/234, 154, 156; 203/DIG. 6, 40, 29, 33, 36, 92, 93, 95–97, 76, 83, 94, 98, DIG. 9; 562/600, 606–609; 162/14–16; 422/193, 195, 197, 189

[56] References Cited

U.S. PATENT DOCUMENTS

| | | | |
|---|---|---|---|
| 939,980 | 11/1909 | Chute | 562/608 |
| 2,070,100 | 2/1937 | Twomey | 202/158 |
| 2,134,882 | 11/1938 | Monro | 202/156 |
| 2,444,527 | 7/1948 | Pomeroy | 203/37 |
| 2,988,347 | 6/1961 | Molique | 202/154 |
| 3,189,531 | 6/1965 | Hack et al. | 202/154 |
| 3,412,016 | 11/1968 | Graven | 203/DIG. 9 |
| 3,506,408 | 4/1970 | Kageyama et al. | 203/DIG. 6 |
| 4,406,745 | 9/1983 | Martel | 202/197 |
| 4,475,005 | 10/1984 | Paret | 203/DIG. 6 |
| 4,818,346 | 4/1989 | Bentham et al. | 202/197 |

Primary Examiner—Wilbur Bascomb
Attorney, Agent, or Firm—Neuman, Williams, Anderson & Olson

[57] ABSTRACT

A process for removing volatile acids from aqueous solutions which involves steam stripping a volatile acid from an aqueous solution and contacting the vaporized acid with a reactable cation to form a salt of the acid. A preferred embodiment of apparatus comprises an elongated distillation column having therein a plurality of zones or stages wherein the volatile acid in the aqueous feed stream is vaporized by steam and then the vaporized acid is carried by the steam into a salt formation zone or stage to react with a reactable cation to form a salt of the acid.

4 Claims, 1 Drawing Sheet

DISTILLATION APPARATUS FOR REMOVAL OF VOLATILE ACIDS FROM AQUEOUS SOLUTIONS

This is a division of application Ser. No. 189228 filed May, 2, 1988, now U.S. Pat. No. 4,898,644 the text of which is hereby incorporated by reference.

This invention relates to removing volatile acids from an aqueous solution thereof.

Disposal of effluent or waste streams from manufacturing processes often presents problems from an environmental or ecological standpoint. Many waste streams from manufacturing processes should not be discharged into natural streams, lakes or rivers because they contain materials which may be considered to be undesirable pollutants. Thus, for example, in the commercial production of furfural the aqueous effluent from the production process contains quantities of the volatile acids acetic acid and formic acid. It is desirable to remove these acids before discharging the effluent to the environment.

It is therefore a principal object of this invention to provide a process for removal of volatile organic acids from aqueous solutions thereof.

It is another object of this invention to provide an efficient process for removal of volatile acids from an aqueous stream with minimization of energy requirements.

Another specific object of this invention is to provide a process for removal of acetic acid from an aqueous solution with recovery of useful salts of acetic acid.

A still further object of this invention is to provide apparatus for efficient removal of volatile acids from an aqueous solution.

In its broad aspect, the process of this invention involves steam stripping a volatile acid from an aqueous solution and contacting the vaporized acid with a reactable cation to form a salt of the acid. In a preferred embodiment, the process of the invention for removing a volatile acid from an aqueous solution thereof comprises flowing an aqueous solution of a volatile acid downwardly through a distillation column and flowing steam upwardly within said column so as to contact and vaporize at least a portion of the volatile acid. The vaporized acid carried by the steam then contacts a cation reactable with said acid to form a salt therewith, and the salt is removed from the column.

It is preferred to utilize a number of steam stripping equilibrium stages so as to increase the amount of acid removed from the acid feed solution. One equilibrium stage comprises a sufficient number of theoretical distillation plates so that the vapor leaving that stage contains an amount of acid that is required to be in equilibrium with the liquid leaving that stage. The number of equilibrium stages required for the steam stripping can vary, depending upon the amount of acid removed in each such stage and the total amount desired to be removed from the acid feed stream.

A preferred embodiment of apparatus for recovering a volatile acid from an aqueous solution in accordance with this invention comprises an elongated distillation column having therein a plurality of zones or stages wherein the volatile acid in the aqueous feed stream is vaporized by steam and then the vaporized acid is carried by the steam into a salt formation zone or stage to react with a reactable cation to form a salt of the acid. The liquid flow through the column is such that the liquid acid feed stream flows only through acid vaporization zones while the reactable cation in a liquid vehicle flows only through the salt formation stages. The acid vaporization zones and salt formation zones are alternately disposed within the distillation column. The column has means for flowing steam upwardly within and inlet means for introducing an aqueous acid solution into the upper part of the column as well as inlet means for introducing an acid-reactive cation in a liquid vehicle such as an aqueous solution or slurry. The column is designed so that the said aqueous acid solution flows downwardly within the column from an acid vaporizing zone to the next lower acid vaporizing zone and counter-currently to the upward flow of steam. Likewise, the liquid containing an acid-reactive cation flows downwardly within said column from a salt formation zone to the next lower salt formation zone.

Thus, the preferred apparatus for use in the invention comprises an elongated distillation column having therein separate liquid-vapor contact zones through which a first and second liquid flow on one or more distillation plates. Means are provided for flowing steam upwardly within said column into contact with all of the liquid-vapor contact zones. Inlet means for introducing a first liquid into the upper part of said column and inlet means for introducing a second liquid into said column are provided. The column is provided with means for flowing said first liquid downwardly within the column and countercurrently to the upward flow of steam in a liquid-vapor contact zone, and it also has means for flowing said second liquid downwardly within said column and counter-currently to the upward flow of steam in a liquid-vapor contact zone separate from the liquid-vapor zone in which said first liquid flows.

The invention will be described in detail in conjunction with the drawings in which.

Figure 1:
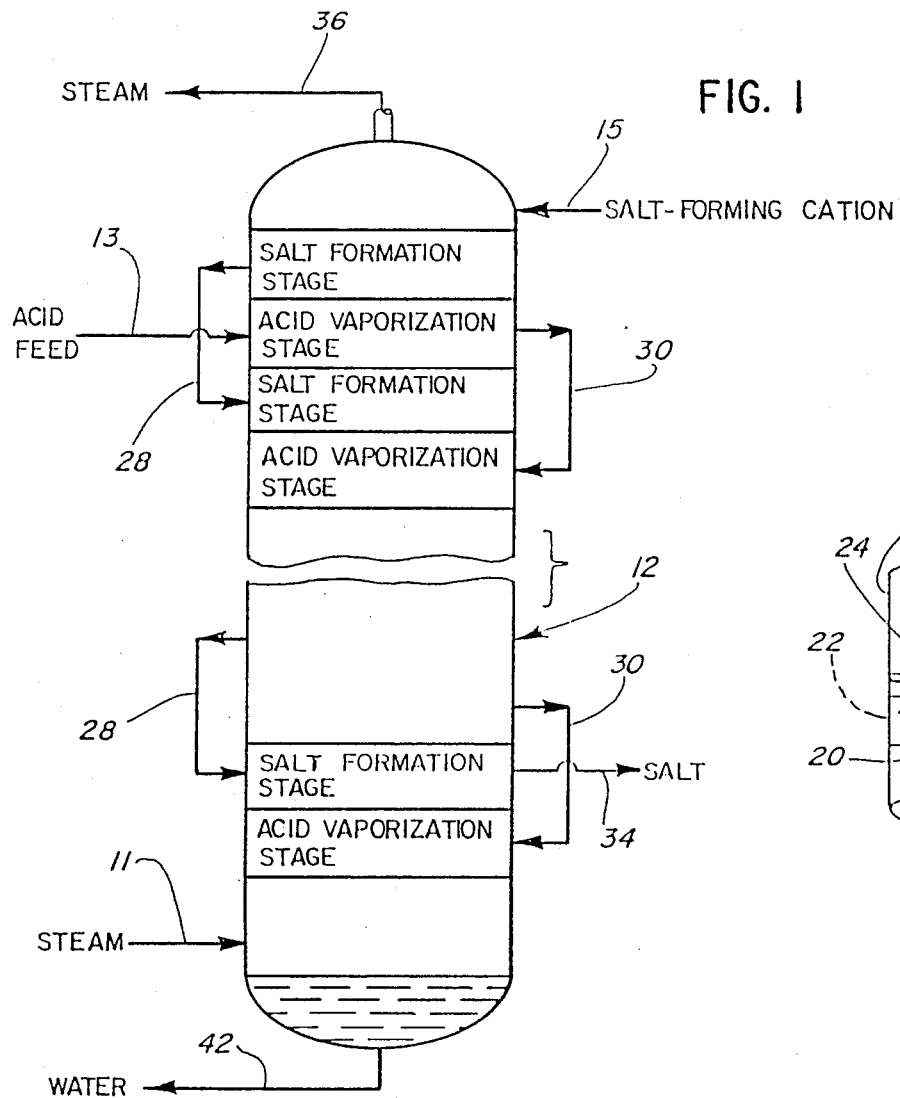
FIG. 1 is a schematic view of preferred distillation apparatus for vaporizing acid from the feed and subjecting the vaporized acid to salt formation.
Figure 2:
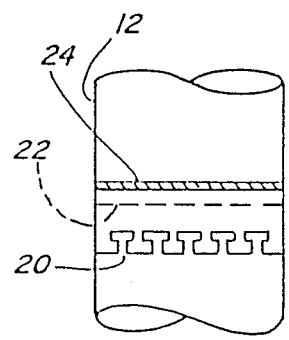
FIG. 2 is a schematic partial view showing a preferred arrangement of distillation plates within the distillation apparatus.

Referring to FIG. 1, steam is supplied through conduit 11 to distillation column 12 and flows upwardly through the column. An aqueous feed stream containing a volatile acid or mixture of acids, such as acetic acid and formic acid, is introduced through line 13 at a location in the upper portion of column 12. A cation reactive with the acid is introduced into the stripping column 12 through line 15, preferably in a liquid carrier vehicle such as an aqueous solution or slurry.

In the preferred apparatus of this invention, bubble-cap trays 20 of known type are employed as the bottom distillation plate in each stage of the process, that is, in both the acid vaporization stages and the salt formation stages. Bubble-cap trays minimize "weeping", i.e., the leaking of liquid from the bottom surface as occurs in a distillation tray of perforated type. For economy, conventional metallic perforated distillation plates 22 can be used above each bubble-cap tray. Also, known demister means, such as wire mesh screens 24, are preferably used above each distillation plate 22 in the acid vaporization zones to increase the efficiency of the steam stripping by minimizing entrainment of liquid.

The aqueous acid feed stream and the cation containing liquid flow downwardly through the distillation column through alternately arranged acid vaporizing stages and salt formation stages, respectively. Conventional downcomers 28 are employed to direct the liquid cation stream downwardly to the next lower salt formation stage while downcomers 30 direct flow of the liquid acid stream downwardly from one acid vaporization zone to the next lower acid vaporization zone, by-passing the intermediate salt formation zone. The downcomers 28 and 30 can be disposed internally or externally of the distillation column 12. Steam flows upwardly within distillation column 12 counter-currently to the liquid acid stream and the cation-containing liquid. The upwardly flowing steam strips the volatile acid from the aqueous acid stream and then the steam and acid vapors flow upwardly into contact with the cation-containing liquid flowing on a superposed distillation tray in a salt formation zone or stage.

Equilibrium reaction between the acid vapors and the reactable cation results in the formation of a salt of the acid. The acid salts carried by the downwardly flowing liquid are removed from the lower end of the distillation column 12 through conduit 34. Steam from which the acid has been removed by salt formation leaves the top of the column through line 36 and can be recycled, or used elsewhere where a steam supply is required water can be removed from the bottom of column 12 through line 42.

The acid reactable cation which is introduced into the distillation column 12 through line 15, preferably in a liquid carrier vehicle can be an acid reactable alkaline material such as sodium hydroxide, sodium carbonate, calcium hydroxide, calcium carbonate, potassium hydroxide, magnesium hydroxide, magnesium carbonate and the like. The pH of the cation-containing liquid introduced into the column through line 15 is generally preferred to be above the titration value of the acid salt which, in the case of acetic acid, is generally in the range of about 8.0 to 8.6 pH. The cation is employed in amounts to provide at least one neutralization equivalent per equivalent of acid or acids.

Figure 3:
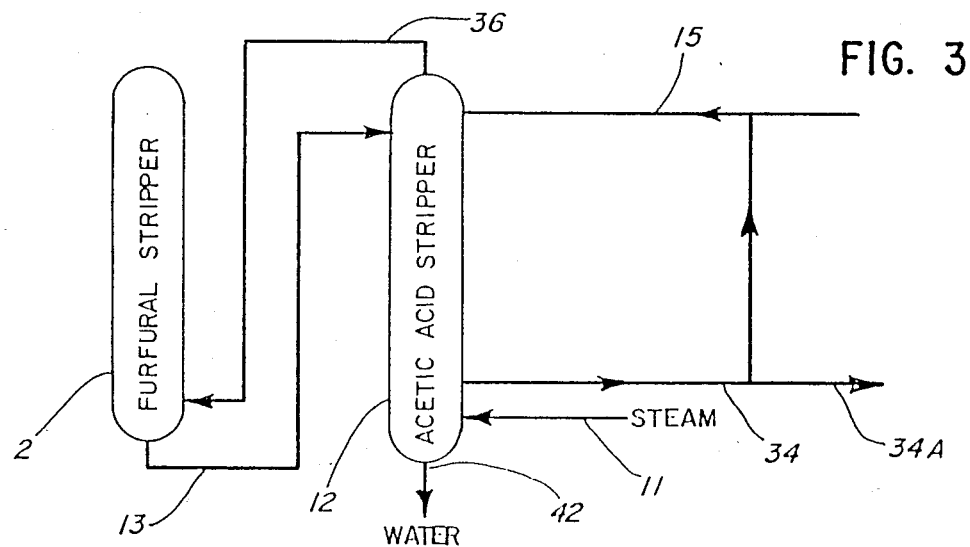
FIG. 3 is an illustrative flow diagram of a process for removing a volatile acid in accordance with this invention.

The following represents a specific illustrative example of the process of the present invention described in conjunction with FIG. 3 of the drawing, which is an illustrative flow diagram. The bottoms effluent from a furfural steam stripper 2 is transferred via line 13 into the acetic acid stripper column 12 near the top thereof. This effluent stream from the furfural stripper typically contains about 1% by weight of volatile acids, principally acetic acid and formic acid, in a ratio of 9:1. In a typical operation, the acetic acid containing stream from the furfural stripper flows at a rate of about 400 gallons per minute (200,000 pounds per hour) at a temperature of 225° F. and under a pressure of about 5 psig.

A cation reactive with the acid in a liquid carrier, such as, for example, a 50% by weight calcium hydroxide slurry, is pumped into the stripper column 12 through line 15 at a rate of approximately 200 gallons per minute and at a temperature of 225° F.

Steam is injected into the lower part of the acetic acid stripper 12 through line 11 at a rate of approximately 40,000 pounds per hour at a pressure of 10-15 psig. Thus, the steam flow is about 20% of the flow of the acid feed stream which flows downwardly through stripping column 12 in alternate acid vaporization zones. When the upwardly flowing steam contacts the liquid acid stream, a portion of the acid is vaporized and transferred to the steam, the amount vaporized depending upon the vapor pressures of the acid. Then the acid-loaded steam contacts the cation-containing liquid flowing in a superposed salt formation stage with the result that salts of the acids are formed. The so-formed salts become concentrated at each stage of salt formation and the salts are removed from the stripper column 12 through line 34. Steam, essentially free of acid, is removed via line 36 and recycled to the furfural stripping operation 2.

Initially all of the alkaline solution flowing from line 34 is recycled back to line 15. Then, after the system is in operation and equilibrium operation achieved, only a minor portion of the salt is removed through line 34A and a major portion of the acid salt stream exiting through line 34 is recycled to line 15 as the cation feed. In such operation, fresh makeup cation will be introduced through line 15 at approximately the same rate as salt is recovered from the system through line 34A. Thus, for example, if the rate of removal of acetate and formate salts through line 34A is at the rate of 3 gallons per minute, fresh makeup cation is supplied through line 15 at approximately the same rate.

Acetate salts have different uses. For example, calcium acetate and/or magnesium acetate find increasing use in street and road de-icing operations.

Acetic acid is somewhat less volatile than water, so the amount present in the steam is about 70% of that in the liquid acid stream, at equilibrium, i.e., relative volatility = 0.692, at 1 atmosphere. With the 1:5 steam:acid feed flow employed in this example, this will result in about 12% removal of acetic acid as vapor per equilibrium stage, with 88% remaining in the liquid phase. With 88% remaining in liquid after one equilibrium stage, two equilibrium stages will result in 0.88×0.88 or 77.4% remaining in the liquid. The following chart shows the number of equilibrium stages required for removal of various amounts of acetic acid from the aqueous acid stream under the said flow conditions.

| Number of Equilibrium Stages | Theoretical Distillation Plates* | Acetic Acid % Remaining In Liquid | % Acetic Acid Vapor |
| --- | --- | --- | --- |
| 1 | 4 | 88 | 12 |
| 2 | 8 | 77.4 | 22.6 |
| 4 | 16 | 60.0 | 40.0 |
| 8 | 32 | 36. | 64. |
| 16 | 64 | 12.9 | 87.1 |
| 32 | 128 | 1.7 | 98.3 |

*At 50% efficiency per plate, i.e. 2 plates for each acid vaporization stage and 2 plates for each salt formation stage.

By virtue of the process of this invention, low pressure steam can be used to remove substantially completely volatile organic acids from aqueous solutions thereof. The steam can be recovered and thus the process is both effective and economical.

While the present invention has been described in detail with reference to removal of acetic acid and formic acid from aqueous solutions, it will be apparent that other volatile acids can be likewise removed from aqueous solutions. Those modifications and equivalents which fall within the spirit of the invention are to be considered a part thereof.

What is claimed is:

1. Apparatus for removing a volatile component from an aqueous solution comprising:

an elongated distillation column having therein separate vertically and alternately disposed liquid-vapor contact zones through which a first and second liquid flow,
one or more distillation plates within each of said liquid-vapor contact zones,
means for introducing steam at the lower end of said column for upward flow therein into contact with all of the liquid-vapor contact zones,
inlet means for introducing a first liquid into the upper part of said column,
inlet means for introducing a second liquid into said column,
means for flowing said first liquid downwardly within said column and countercurrently to the upward flow of steam in a liquid-vapor contact zone,
means for flowing said second liquid downwardly within said column and countercurrently to the upward flow of steam in a liquid-vapor contact zone separate from the liquid-vapor zone in which said first liquid flows,
steam outlet means in the upper portion of said column, and
outlet means in the lower portion of said column for recovering a liquid stream.

2. Apparatus in accordance with claim 1 wherein the bottom distillation plate within each of said zones is of the bubble-cap type.

3. Apparatus in accordance with claim 1 wherein demister means are employed in the liquid-vapor contact zones.

4. Apparatus in accordance with claim 1 wherein a downcomer connects a liquid-vapor contact zone through which said first liquid flows to a lower liquid-vapor contact zone through which said first liquid flows and a downcomer connects a liquid-vapor contact zone through which said second liquid flows to a lower liquid-vapor contact zone through which said second liquid flows.

* * * * *

UNITED STATES PATENT AND TRADEMARK OFFICE
CERTIFICATE OF CORRECTION

PATENT NO. : 4,917,769

DATED : April 17, 1990

INVENTOR(S) : Wendell E. Van Horn

It is certified that error appears in the above-identified patent and that said Letters Patent is hereby corrected as shown below:

Column 3, line 27, insert a period (.) after "required"

line 27, "water" should be -- Water --

Signed and Sealed this

Sixth Day of August, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,917,769
DATED : April 17, 1990
INVENTOR(S) : Wendell E. Van Horn It is certified that error appears in the above-identified patent and that said Letters Patent is hereby corrected as shown below:

On the title page, item [73] Assignee:
should be "QO Chemicals, Inc."

Signed and Sealed this

Twentieth Day of October, 1992

Attest:

DOUGLAS B. COMER

*Attesting Officer*   Acting Commissioner of Patents and Trademarks